United States Patent [19]

Werner et al.

[11] 4,447,647

[45] May 8, 1984

[54] PROCESS FOR THE PREPARATION OF 2,4,6-TRICHLOROANILINE

[75] Inventors: Friedrich Werner, Belford Roxo, Brazil; Karl Mannes; Viktor Trescher, both of Leverkusen, Fed. Rep. of Germany

[73] Assignee: Bayer Aktiengesellschaft, Leverkusen, Fed. Rep. of Germany

[21] Appl. No.: 453,984

[22] Filed: Dec. 28, 1982

[30] Foreign Application Priority Data

Jan. 5, 1982 [DE] Fed. Rep. of Germany ....... 3200069

[51] Int. Cl.³ .............................................. C07C 85/24
[52] U.S. Cl. .................................................... 564/412
[58] Field of Search ......................................... 564/412

[56] References Cited

U.S. PATENT DOCUMENTS 2,675,409  4/1954  Orloff et al. ......................... 564/412

Primary Examiner—Paul F. Shaver
Attorney, Agent, or Firm—Sprung, Horn, Kramer & Woods

[57] ABSTRACT

2,4,6-Trichloroaniline is prepared by reaction of aniline, which is optionally substituted by halogen, with a chlorinating agent in the presence of inert organic solvents and/or diluents at elevated temperatures.

12 Claims, No Drawings

PROCESS FOR THE PREPARATION OF 2,4,6-TRICHLOROANILINE

The invention relates to a process for the preparation of 2,4,6-trichloroaniline by reaction of aniline, which is optionally substituted by halogen, and/or its hydrochloride with a chlorinating agent in the presence of inert organic solvents and/or diluents.

The preparation of 2,4,6-trichloroaniline by reaction of aniline or its hydrochloride with chlorine or sulphuryl chloride in the presence of inert organic solvents has been disclosed (compare, for example, Liebigs Ann. Chem. 53, 35 (1845), J. prak. Chem. (2), 16, 449 (1877), Liebigs Ann. Chem. 196, 230 (1879), Ber. 27, 3151 (1894), Ber. 55, 221 (1922), Metody Peluchemia khim. Reaktinov preperatov 26, 280–282 (1974) (cited in CA 83, 113802 v), U.S. Pat. No. 2,675,409). In general, in the processes mentioned, the control of temperature is stated to be of particular importance. Thus, for example, care is taken on mixing the reactants that the temperature does not rise too high, and this can be brought about by cooling the reaction mixture (compare, for example, Liebigs Ann. Chem. 196, 231 (1879)). Although the reaction mixture is usually then heated to a somewhat higher temperature to complete the reaction, it is expressly pointed out in Ber. 55, 221 (1922) that the temperature of the reaction mixture should not exceed 70° C. In U.S. Pat. No. 2,675,409, it is in fact mentioned in column 3, lines 29 to 33, that the temperature for the chlorination is rather unimportant, but in practice temperatures of 0° to 40° C. are employed.

The disadvantages of the processes mentioned are the yields of 2,4,6-trichloroaniline, which are unsatisfactory for a large-scale industrial process, and, in addition, the substance is frequently contaminated with by-products to a considerable extent, which necessitates cost-intensive subsequent purification.

It is in fact reported, in Ber. 55, 221 (1922) (see Example 2), that pure 2,4,6-trichloroaniline is obtained in a yield of 90 to 95% of theory starting from aniline hydrochloride. However, this report could not be confirmed in a recent repetition of the process (compare Metody Peluchemia khim. Reaktinov preperatov 26, 280–282 (1974)). In the repetition, a yield of only about 60% of pure 2,4,6-trichloroaniline was obtained. Furthermore, the yield of 92% of 2,4,6-trichloroaniline reported in the example in U.S. Pat. No. 2,675,409 only relates to a heavily contaminated crude product, the content of 2,4,6-trichloroaniline of which is only about 65%, as our own comparison experiments show (see comparison example).

A general process for the chlorination of anilines at temperatures from 10° to 80° C. is described in German Offenlegungsschrift No. 2,449,285. However, it is expressly pointed out (compare page 4, 2nd paragraph in the German Offenlegungsschrift), that a relatively large proportion of higher chlorinated products should be avoided. This governs the molar ratios of amine employed to chlorine employed reported in this reference. According to Example 2 in the German Offenlegungsschrift mentioned, on chlorinating aniline in chlorobenzene at 27° to 32° C., a mixture of products is obtained, which only contains a minor proportion of 2,4,6-trichloroaniline.

A process has now been found for the preparation of 2,4,6-trichloroaniline by reaction of anilines of the formula

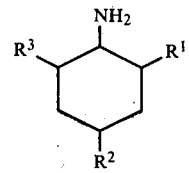

wherein
$R^1$, $R^2$ and $R^3$ are identical or different and represent hydrogen or halogen, and at least one of the radicals denotes hydrogen,
and/or their hydrochlorides, with a chlorinating agent in the presence of inert organic solvents and/or diluents, which is characterized in that the reaction is carried out at temperatures above 80° C.

Halogens which may be mentioned are: chlorine, bromine and iodine, preferably chlorine.

Examples of suitable starting products for the process according to the invention are: aniline, 2-chloroaniline, 4-chloroaniline, 2,4-dichloroaniline or 2,6-dichloroaniline, preferably aniline.

The process according to the invention is generally carried out at temperatures from about 82° to 180° C., preferably at 85° to 175° C., particularly preferably at 90° to 170° C.

Chlorinating agents which can be employed in the process according to the invention include: nitrogen trichloride, N,N-dichloroethylamine, N,2,4-trichloroacetanilide, sulphuryl chloride and/or elementary chlorine, preferably elementary chlorine and/or sulphuryl chloride.

The chlorinating agents are generally employed in the process according to the invention in a small molar excess. However, it is also possible to employ the chlorinating agent in equivalent amounts, relative to the starting product. Customarily, the chlorinating agent is employed in a molar excess of about 1 to 20 mol%, preferably 5 to 15 mol%, per chlorine to be introduced.

Those inert organic solvents and/or diluents can be employed which are inert under the reaction conditions. Examples which may be mentioned are: chlorobenzene, o-, m- and p-dichlorobenzene, trichlorobenzene, nitrobenzene, 1,1,1-trichloroethane and/or carbon tetrachloride. However, it is also possible to employ 2,4,6-trichloroaniline itself as a solvent in the process according to the invention.

The amount of the inert organic solvent and/or diluent is not critical and can vary within wide limits. The process can be carried out both at high dilution and also at high concentrations. In general, about 0.1 to 50 parts, preferably 1 to 10 parts, of inert organic solvent and/or diluent are used to one part of aniline employed.

The process according to the invention can be carried out in such a manner that the starting product is introduced into an inert organic solvent and/or diluent, the mixture is heated up to the desired reaction temperature and the chlorinating agent is then added. If necessary, after the end of the reaction, the reaction mixture is subsequently heat-treated to destroy the hydrochlorides. Temperatures of about 80° to 250° C., preferably 90° to 150° C., e.g., 95° to 150° C., are suitable for this purpose. Thereafter, the solvent and/or diluent is distilled off and the crude 2,4,6-trichloroaniline obtained is converted into virtually pure 2,4,6-trichloroaniline by distillation of sublimation. Of course, it is also possible to treat the reaction mixture by water washing, according to the state of the art, in order to bring about hydrolytic cleavage of the hydrochlorides. However, this is elaborate and of little benefit.

Another possibility of preparing 2,4,6-trichloroaniline in a particularly economic manner consists in initially introducing the inert organic solvent and/or diluent with only a part of the starting product (about 0.001 to 40% by weight, preferably 1 to 20% by weight, relative to the total amount of aniline derivative to be reacted) and adding the rest of the starting product synchronously with the total amount of chlorinating agent. Obviously, it is also possible to meter the total amount of starting product synchronously with the total amount of chlorinating agent into the initially introduced inert organic solvent and/or diluent, that is to say without initially introducing even a part of the starting product.

In this variant, temperatures in the range from about 20° to 180° C., advantageously at 60° to 175° C., very particularly preferably at 80° to 160° C., can be employed.

The process according to the invention can be carried out both continuously and also discontinuously.

Compared to the state of the art, 2,4,6-trichloroaniline is obtained by the process according to the invention in a better yield, a higher space-time yield and of a better product quality. This is all the more surprising since it was necessary to assume, from the state of the art, that at higher reaction temperatures, on using the free aniline derivative and by the heat treatment of the crude mixture, the product quality and the yield of 2,4,6-trichloroaniline would be reduced.

The process according to the invention may be illustrated by means of the examples below, but without restricting it to these examples.

COMPARISON EXAMPLE (ACCORDING TO U.S. Pat. No. 2,675,409)

1.0 mol of aniline is treated with chlorine according to Example 1 in U.S. Pat. No. 2,675,406. 176 g of crude 2,4,6-trichloroaniline, having a content of pure 2,4,6-trichloroaniline of 67.8% (yield: 60.7%; determined by HPLC, high pressure liquid chromatography) are obtained. The crude 2,4,6-trichloroaniline contains 0.5% of trichlorophenol, 1.5% of tetrachlorophenol, 1.5% of pentachlorophenol, 4 to 5% of unknown compounds and about 20% of polymers.

EXAMPLE 1

96 g of aniline are dissolved in 750 ml of chlorobenzene. 40 g of HCl gas are passed into the solution and it is then heated to 90° C. 432 g of sulphuryl chloride are added dropwise, with efficient stirring, within 6 hours. The mixture is stirred at 90° C. for a further 15 minutes and then at 130° C. for a further hour. Chlorobenzene is distilled off and 204 g of crude trichloroaniline are obtained (86.3% pure), (HPLC)=89.5% of theory. Sublimation of the crude product provides 176 g of 2,4,6-trichloroaniline (97.2% pure) (HPLC).

EXAMPLE 2

The reaction is carried out in analogy to Example 1 at 110° C. 192 g of crude trichloroaniline, 89.1% pure=87.5% of theory, are obtained.

EXAMPLE 3

The reaction is carried out in analogy to Example 1. 750 ml of o-dichlorobenzene serve as the solvent. 191 g of crude 2,4,6-trichloroaniline, 91.3% pure=88.7% of theory, are obtained. After sublimation, 176 g of trichloroaniline, having a content of 98.7%, are obtained.

EXAMPLE 4

36 g of aniline are dissolved in 500 ml of chlorobenzene in a 2 l three-neck flask. 15 g of gaseous hydrogen chloride are passed in. The solution is then heated to 110° C. 864 g of sulphuryl chloride, at 108 g h$^{-1}$, and 170 g of aniline, at 21.3 g h$^{-1}$, are introduced synchronously within 8 hours. After this introduction, the mixture is stirred at 130° C. for 1 hour. Then chlorobenzene is distilled off under increasing waterpump vacuum. 407 g of crude 2,4,6-trichloroaniline, 89.9% pure=93.1% of theory, are obtained. The product contains, apart from residues of chlorobenzene, 1% of tetrachloroaniline and 6% of polymers. The yield of pure (98.2% pure) product after sublimation is 366.2 g.

EXAMPLE 5

93 g of aniline are dissolved in 850 ml of chlorobenzene. 40 g of HCl gas are passed in at room temperature and the mixture is then heated to 90° C. 231 g of chlorine are passed in within 8 hours. The mixture is then stirred at 130° C. for 1 hour and chlorobenzene is distilled off under waterpump vacuum. 209 g of crude 2,4,6-trichloroaniline, 81.8% pure (HPLC)=87.0% of theory, are obtained. The yield of pure product (96% pure) after sublimation is 175 g.

EXAMPLE 6

63.8 g of o-chloroaniline are dissolved in 375 ml of chlorobenzene. 20 g of hydrochloric acid gas are passed in and the mixture is heated to 110° C. 139.5 g of sulphuryl chloride are allowed to run in within 6 hours. The mixture is then stirred at 130° C. for 1 hour and chlorobenzene is distilled off until the bottom temperature reaches 110° C. under 20 mbar. 100 g of 2,4,6-trichloroaniline, having a content of 84.3%=85.4% of theory, are obtained.

EXAMPLE 7

The amounts and the procedure are analogous to Example 5, but the temperature was maintained at 100° C. 210 g of 2,4,6-trichloroaniline, 87.4%=93.4% of theory, are obtained. The yield of pure product (97.6% pure) is 186 g.

EXAMPLE 8

37.2 g of aniline are added to 500 ml of chlorobenzene. Then 17.0 g of HCl gas are passed in with cooling. The mixture is heated to 100° C. 462 g of chlorine and 148.8 g of aniline are metered in synchronously within 8 hours. The mixture is heated up to 110° C. for 1 hour and then chlorobenzene is distilled off until the bottom reaches a temperature of 80° C. under 20 mbar. 410 g of crude trichloroaniline are obtained. 370.3 g of 97.2% pure product are obtained after sublimation (91.6% of theory).

EXAMPLE 9

17.0 g of HCl gas are passed into a mixture of 37.2 g of aniline and 1500 ml of chlorobenzene. The mixture is heated to 50° C. 497 g of chlorine and 148.8 g of aniline are metered in synchronously within 8 hours. For the thermal decomposition of the hydrochlorides, the mixture is heated to 130° C. and stirred at this temperature for 1 hour. The chlorobenzene is distilled off until the bottom reaches 80° C. under 20 mbar. 409 g of crude 2,6-trichloroaniline, 77.2% pure=80.3% of theory, are obtained.

EXAMPLE 10

7 g of aniline are initially introduced in 650 ml of chlorobenzene and heated to 100° C. At this temperature, 552.5 g of chlorine and 226 g of aniline are metered in synchronously within 20 hours.

After stirring at 130° C. for one hour, the chlorobenzene is distilled off in vacuo.

480 g of trichloroaniline (crude), having a content of 89.1%, corresponding to 87% of theory, are obtained.

What is claimed is:

1. A process for the preparation of 2,4,6-trichloroaniline which comprises contacting an aniline of the formula

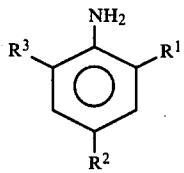

wherein $R^1$, $R^2$ and $R^3$ independently represent hydrogen or halogen and at least one of the radicals denotes hydrogen, and/or their hydrochlorides, with a chlorinating agent in the presence of an inert organic solvent or diluent at a temperature above 80° C.

2. A process according to claim 1 wherein the process is carried out at a temperature of 82° to 180° C.

3. A process according to claim 1 wherein the process is carried out at a temperature of 85° to 175° C.

4. A process according to claim 1 wherein the process is carried out at a temperature of 90° to 170° C.

5. A process according to claim 1 wherein the process is carried out at a temperature of 95° to 170° C.

6. A process according to claim 1 wherein the process is carried out by initially introducing said inert organic solvent or diluent together with a portion of the aniline reactant to a reaction vessel and thereafter the balance of the aniline reactant and chlorinating agent are introduced to the reaction vessel synchronously.

7. A process according to claim 6 wherein said inert organic solvent or diluent is initially introduced together with 0.001 to 40% by weight of said aniline reactant, relative to the total amount of aniline reactant to be reacted, and the balance of the aniline reactant is added synchronously with the total amount of chlorinating agent.

8. A process according to claim 6 wherein said inert organic solvent or diluent is initially introduced to the reaction vessel together with 1 to 20% by weight of aniline reactant to be reacted, based upon the total amount of aniline reactant to be reacted, and the balance of the aniline reactant is added synchronously together with the total amount of chlorinating agent.

9. A process for the preparation of 2,4,6-trichloroaniline which comprises contacting an aniline reactant of the formula

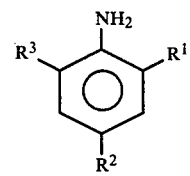

wherein $R^1$, $R^2$ and $R^3$ are identical or different and represent hydrogen or halogen, and at least one of the radicals denotes hydrogen, and/or their hydrochlorides, with a chlorinating agent in the presence of an inert organic solvent or diluent by introducing the inert organic solvent or diluent initially together with a part of the aniline reactant to a reaction vessel and thereafter adding the balance of the aniline reactant and the chlorinating agent synchronously and carrying out the process at a temperature of 20° to 180° C.

10. A process according to claim 9 wherein the process is carried out at a temperature of 60° to 175° C.

11. A process according to claim 9 wherein the inert solvent or diluent is initially introduced with 0.001 to 40% by weight of the aniline reactant to be reacted, based upon the total amount of aniline reactant to be reacted, and the balance of the aniline reactant is added synchronously together with the total amount of chlorinating agent.

12. A process according to claim 9 wherein said inert organic solvent or diluent is initially introduced to the reaction vessel together with more than 20% by weight of aniline reactant to be reacted, based upon the total amount of aniline reactant to be reacted, and the balance of the aniline reactant is added synchronously with the total amount of chlorinating agent.

* * * * *